(12) United States Patent
Faustmann et al.

(10) Patent No.: US 9,121,816 B2
(45) Date of Patent: Sep. 1, 2015

(54) APPARATUS FOR DETERMINING THE PROPERTIES OF A MEDIUM IN THE FORM OF A FLUID OR A SOFT MATERIAL

(75) Inventors: Hendrik Faustmann, Coburg (DE); Michael Muench, Coburg (DE)

(73) Assignee: SENSACTION AG, Coburg (DE)

( * ) Notice: Subject to any disclaimer, the term of this patent is extended or adjusted under 35 U.S.C. 154(b) by 325 days.

(21) Appl. No.: 13/321,861

(22) PCT Filed: May 17, 2010

(86) PCT No.: PCT/EP2010/056717
§ 371 (c)(1),
(2), (4) Date: Nov. 22, 2011

(87) PCT Pub. No.: WO2010/136350
PCT Pub. Date: Dec. 2, 2010

(65) Prior Publication Data
US 2012/0060591 A1   Mar. 15, 2012

(30) Foreign Application Priority Data

May 25, 2009   (DE) .......................... 10 2009 022 492

(51) Int. Cl.
*G01N 29/02*   (2006.01)
*G01N 29/24*   (2006.01)
(Continued)

(52) U.S. Cl.
CPC .......... *G01N 29/2462* (2013.01); *G01N 29/032* (2013.01); *G01N 2291/022* (2013.01); *G01N 2291/048* (2013.01); *G01N 2291/0423* (2013.01)

(58) Field of Classification Search
USPC ......... 73/861.18, 861.25, 861.27, 64.53, 628; 264/279
See application file for complete search history.

(56) References Cited

U.S. PATENT DOCUMENTS

| 4,296,348 A | 10/1981 | Toda |
| 4,331,025 A | 5/1982 | Ord |

(Continued)

FOREIGN PATENT DOCUMENTS

| CN | 1229469 A | 9/1999 |
| DE | 29 33 315 C2 | 4/1982 |

(Continued)

OTHER PUBLICATIONS

Nyborg, "Acoustic streaming", in Physical Acoustics 2B, Mason, Academic Press, San Diego, 1965, p. 265-330.

(Continued)

*Primary Examiner* — Peter Macchiarolo
*Assistant Examiner* — Alexander Mercado
(74) *Attorney, Agent, or Firm* — Maschoff Brennan

(57) ABSTRACT

An apparatus determines the properties of a medium in the form of a fluid or soft material. An acoustic waveguide has two opposing guide elements delimiting an interior space to be filled with a medium. The guide elements, upon filling the interior space with a medium, form an interface with the medium with an inner surface. A transmitter generates acoustic surface waves in the waveguide, which are received by a receiver. The waveguide can be coupled with an evaluation unit for determining physical properties of the medium based on a signal generated by the receiver. A housing accommodates the guide elements, transmitter and receiver. On the respective inner surface, at least a part of the acoustic surface waves can be converted into volumetric sound waves of the medium and at least a part of the volumetric sound waves can be converted into acoustic surface waves of the waveguide.

20 Claims, 1 Drawing Sheet

(51) Int. Cl.
*G01N 29/032* (2006.01)
*B29C 39/10* (2006.01)

(56) References Cited

U.S. PATENT DOCUMENTS

| | | | |
|---|---|---|---|
| RE32,859 | E | 2/1989 | Marshall et al. |
| 4,893,496 | A * | 1/1990 | Bau et al. ................... 73/32 A |
| 4,949,583 | A * | 8/1990 | Lang et al. ............... 73/861.357 |
| 5,283,037 | A | 2/1994 | Baer et al. |
| 5,660,528 | A | 8/1997 | Tsunenari |
| 6,010,316 | A | 1/2000 | Haller et al. |
| 6,216,544 | B1 | 4/2001 | Adachi et al. |
| 6,407,479 | B1 * | 6/2002 | Moellendorf et al. .... 310/313 A |
| 6,418,796 | B1 * | 7/2002 | Baumoel .................... 73/861.28 |
| 6,513,365 | B1 * | 2/2003 | Bruetting et al. ............ 73/32 A |
| 6,543,274 | B1 | 4/2003 | Herrmann et al. |
| 6,575,043 | B1 * | 6/2003 | Huang et al. ............... 73/861.25 |
| 6,720,710 | B1 * | 4/2004 | Wenzel et al. ................ 310/328 |
| 6,750,633 | B2 | 6/2004 | Schreiber |
| 6,854,338 | B2 * | 2/2005 | Khuri-Yakub et al. .... 73/861.27 |
| 7,010,962 | B2 * | 3/2006 | Sinha ........................... 73/54.15 |
| 7,077,012 | B2 * | 7/2006 | Hirayama et al. ......... 73/861.25 |
| 7,208,123 | B2 | 4/2007 | Knollenberg et al. |
| 7,360,448 | B2 * | 4/2008 | Maginnis et al. .......... 73/861.27 |
| 7,395,711 | B2 | 7/2008 | Greenwood |
| 8,026,699 | B2 | 9/2011 | Schreiber |
| 2004/0031322 | A1 | 2/2004 | Greenwood |
| 2007/0034016 | A1 * | 2/2007 | Maginnis et al. .......... 73/861.28 |
| 2008/0260582 | A1 | 10/2008 | Gauer et al. |
| 2009/0007694 | A1 * | 1/2009 | Breeuwer .................. 73/861.25 |
| 2009/0025487 | A1 * | 1/2009 | Gysling et al. ............. 73/861.25 |
| 2009/0322086 | A1 | 12/2009 | Letas |
| 2012/0055263 | A1 * | 3/2012 | Konzelmann .............. 73/861.18 |
| 2012/0285260 | A1 * | 11/2012 | Mueller et al. ............. 73/861.27 |

FOREIGN PATENT DOCUMENTS

| | | |
|---|---|---|
| DE | 197 25 012 C1 | 11/1998 |
| DE | 10 2004 051 394 B4 | 8/2006 |
| DE | 10 2007 045 136 A1 | 3/2008 |
| EP | 0 212 470 A2 | 3/1987 |
| EP | 0 988 538 B1 | 2/2002 |
| EP | 1 413 858 A1 | 4/2004 |
| JP | 2002-178507 A | 6/2002 |
| JP | 2005-282541 A | 10/2005 |
| WO | 98/57163 A1 | 12/1998 |
| WO | 02/077635 A2 | 10/2002 |
| WO | 2008/034878 A2 | 3/2008 |

OTHER PUBLICATIONS

Lighthill, "Acoustic streaming", Journal of Sound and Vibration 61/3, 1978, p. 391-418.
Nyborg, "Acoustic streaming", in Nonlinear Acoustics, Hamilton, and Blackstock, Academic Press, San Diego, 1998, p. 207-231.
Wixforth, "Acoustically driven planar microfluidics", Superlattices and Microstructures 33, 2003, p. 389-396.
White, "Surface Elastic Waves", Proceedings of the IEEE, vol. 58, No. 8, Aug. 1970, p. 1238-1276.
Faustmann et al., "Measurement of the properties of liquids based on the dispersion of Lamb waves in an acoustic waveguide", Ultrasonics, Jan. 11-17, 2009.
Moroney et al., "Fluid Motion produced by ultrasonic Lamb waves", Ultrasonics Symposium Proceedings, vol. 1, pp. 355-358, 1990.
Moroney et al., "Microtransport induced by ultrasonic Lamb waves", Appl. Phys. Lett. 59 (1991) 774.
Bradley et al., "Acoustically driven flow in flexural plate wave devices: theory and experiment", Proc. 1994 Ultrasonics Symposium, p. 593-597.
Dohner, "The analysis of a micro-scale pump which uses controlled acoustic streaming for fluid locomotion", Scandia National Laboratories, Sandia report, 1978.
Frampton et al., "The Scaling of Acoustic Streaming for Application in Micro-Fluidic Devices", Applied Acoustics 64 (2003) 681-692.
Frampton et al., "Acoustic streaming in micro-scale cylindrical channels", Applied Acoustics 65 (2004) 1121-1129.
Lindner et al., "Digital Precision Measurement of Force, Pressure and other Mechanical Quantities with an Acoustic Waveguide Sensor", Sensor Conference, 2007.
Balasubramaniam et al., "High temperature ultrasonic sensor for the simultaneous measurement of viscosity and temperature of melts", vol. 70, No. 12, Dec. 1, 1999, p. 4618-4623.
G. Lindner et al.: "5K-5 A Versatile Acoustic Waveguide Sensor for Liquids based on Multiple Mode Conversion at Solid-Liquid Interfaces", Ultrasonics Symposium, 2006, IEEE, IEEE, PI LNKD-DOI:10.1109/ULTSYM.2006.303, Oct. 1, 2006; pp. 1181-1184, XP031076507, ISBN: 978-1-4244-0201-4.
L. C. Lynnworth; "Ultrasonic Measurements for Process Control: Theory, Techniques, Applications" Academic Press Sep. 11, 1989; pp. 112-113 & 398-399.
Nam-Trung Nguyen; "Mikrofluidik: Entwurf, Herstellung Und Charakterisierung" Teubner, 2004; Chapters 6.1 and 6.1.1.
Lindner et al., Messung von Flüssigkeitseigenschaften mit einem flexible konfigurierbaren akustischen Wellenleiter-Sensor; im Tagungsband Sensoren and Messsysteme2006: 13.ITG/GMA Fachtagung vom 13. bis 14. März 2006 p. 269-273, 2006; Abstract.

* cited by examiner

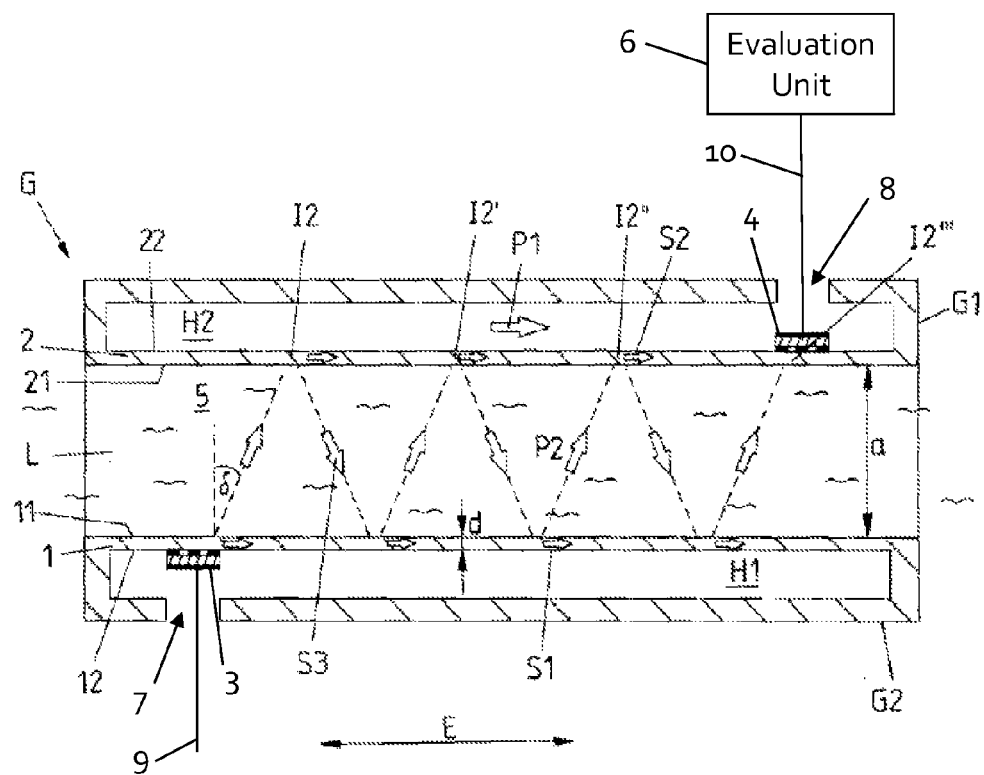

APPARATUS FOR DETERMINING THE PROPERTIES OF A MEDIUM IN THE FORM OF A FLUID OR A SOFT MATERIAL

CROSS-REFERENCE TO A RELATED APPLICATION

This application is a National Phase patent application of International Patent Application Number PCT/EP2010/056717, filed on May 17, 2010, which claims priority of German Patent Application Number 10 2009 022 492.0, filed on May 25, 2009.

BACKGROUND

The present invention relates to an apparatus for determining the properties of a medium in the form of a fluid or a soft material, in particular a highly viscous, dough-like or pasty medium.

A generic apparatus is described in WO 2008/034878 A2. It includes an acoustic waveguide which is formed by at least two opposing guide elements in the form of two plates and encloses an interior space which is filled with the medium to be measured. For filling the interior space and for carrying out measurements, in order to determine the properties of the medium, the waveguide for example is immersed into the medium or the medium is filled into the interior space of the waveguide or guided through the same.

Via a transmitter, acoustic surface waves are generated in the waveguide, wherein at least a part of the energy of the acoustic surface waves is coupled into the medium, so that a part of the energy of the acoustic surface waves is converted into volumetric sound waves of the medium.

Due to the reciprocity of this coupling process between a plate of the waveguide sensor and the medium, a part of the volumetric sound waves propagating in the medium is again coupled back into one or both of the plates of the waveguide, so that acoustic surface waves are generated therein. By measuring and evaluating certain characteristics of these acoustic surface waves, such as their velocity or their amplitudes, chemical and/or physical properties of the medium can be determined.

In principle, the volumetric sound waves are coupled out into the medium under an angle δ relative to a vertical reference line of a plate of the waveguide:

$$\delta = \arcsin(c_M/c_S).$$

Herein, $c_M$ is the sound velocity of the volumetric sound waves inside the medium and $c_S$ is the sound velocity of the acoustic surface waves propagating along a plate of the acoustic waveguide.

In the apparatus described in WO 2008/034878 A2, the (carrier) plates or guide elements of the waveguide sensor are arranged separate from each other at a housing carrying the same. The plates as guide elements of the waveguide each form a sealing cover for a cavity opposite the interior space to be filled with the medium. In this cavity, a transmitter and/or a receiver for generating or receiving the acoustic surface waves are arranged and possibly are directly attached to an outer surface of a guide element facing the cavity.

This form of construction, however, is relatively expensive to manufacture, as it must be ensured that the guide elements guiding the acoustic surface waves seal the cavity associated to them against the entry of the medium. In addition, the design of the separately mounted guide elements with regard to the occurring mechanical loads and for a desired long-term stability of the waveguide formed therewith only can be ensured in a relatively expensive and cost-intensive way.

SUMMARY

Therefore, it is the object underlying the invention to overcome the above-mentioned disadvantages and further improve an apparatus for determining the properties of a medium with a waveguide.

Inside the apparatus according to an exemplary embodiment of the invention it is provided that the guide elements of the acoustic waveguide, which delimit an interior space to be filled with the medium and which each have an inner surface and an outer surface, are integrally formed with a housing in or at which the transmitter and the receiver of the apparatus are accommodated.

With such an inventive integration of the guide elements of the waveguide into the housing, e.g. expensive seals between the guide elements and the housing can be omitted. Due to the one-part design, the mechanical stability of the entire apparatus also is increased. In addition, reflections of acoustic waves can be avoided and an adherence of gas bubbles to the guide element inside the medium can be reduced.

The apparatus according to the invention also involves the advantage that a higher measuring accuracy can be achieved, since a plurality of wave groups of acoustic surface waves can be evaluated therewith.

The guide elements integrally formed with the housing in accordance with the invention preferably not only form an interface with the medium on their inner surface, but also are designed such that on an outer surface of the guide element opposite the inner surface a transmitter and/or a receiver of the apparatus each is arranged, in particular fixed.

In this connection it is furthermore regarded as advantageous that the outer surface of a guide element each borders a cavity of the housing in which the transmitter and/or the receiver is accommodated. Such cavity can be manufactured by a material-removing manufacturing method, such as by turning, milling or boring, inside the housing or a corresponding housing portion initially formed from a solid material. Via a preferably relatively small and hence easily sealed insertion opening, the transmitter and/or the receiver then can be insertable into the interior of the cavity.

Said cavity or said cavities inside the housing, which adjoin the outer surface of the guide elements, preferably are filled with air or another gas or a material which suppresses a decoupling of the sound wave energy from the respective guide element into the adjoining cavity. Instead, the cavities also can be evacuated.

The housing with the integrally molded guide elements of the wave guide also can be an injection-molded or cast part. In a correspondingly alternative design variant, the housing is manufactured by a casting method around the transmitter to be arranged therein and/or the receiver to be arranged therein. This means that when manufacturing the housing, for example the transmitter and/or the receiver of the apparatus already are arranged in a molding die, before the liquid molding material is filled into the molding die for manufacturing the housing. In this way, a cavity can be formed around the transmitter and/or the receiver already during the manufacture of the housing.

Furthermore it is, among other things, also possible that the transmitter and/or the receiver is embedded within a material from which the housing is made. This means, for example, that the transmitter and/or the receiver of the apparatus according to the invention are partly or completely positively arranged inside the housing, in that during the manufacture of the housing the initially liquid material for manufacturing the housing surrounds the transmitter and/or the receiver and subsequently hardens. This is possible in a relatively simple way in particular when manufacturing the housing from plastic material by an injection molding method.

In one exemplary embodiment of the apparatus according to the invention, the housing includes two housing portions in which one of the two opposing guide elements each is integrated or is integrally molded with the associated housing portion. Such housing portions in particular can be two housing halves, between which the interior space for the medium is formed. The medium to be measured can be filled in between the housing portions, or the housing or the housing portions are formed such that between the housing portions the medium to be measured can flow through the waveguide.

In a development of this design variant, the housing or the apparatus according to the invention can be formed such that a distance of the two housing portions from each other and/or an inclination of the two housing portions relative to each other is adjustable.

Preferably, the housing is made of a metal, in particular of stainless steel, or of a plastic material, in particular of a polyether ether ketone (PEEK) or polyoxymethylene (POM). By suitably choosing the material for manufacturing the housing, it is easily possible for example to also use the apparatus according to the invention for determining chemical and/or physical properties of an acidic or alkaline fluid as medium to be measured.

As in accordance with the invention the guide elements guiding the acoustic surface waves need not separately be mounted to the housing and sealed, the waveguide also can easily completely be immersed into the fluid to be measured or into the medium to be measured, in order to fill the interior space of the waveguide located between the two guide elements.

To connect an evaluation unit for determining physical properties of the medium, which possibly lies outside the housing, at least with the receiver of the apparatus, the housing includes at least one cable guide via which a line is guided out of the housing from the receiver located in the interior of the housing. Such (data) line transmits a signal which the receiver generates upon receipt of the acoustic surface waves to the evaluation unit.

Furthermore, it can also be provided that the receiver wirelessly transmits signals to an evaluation unit located outside the housing.

Analogously, it can be provided that a further (control) line for actuating the transmitter is laid through a further or the same cable guide.

The lines partly accommodated in one or more cable guides also can be current-carrying lines for supplying the transmitter or receiver with electric current.

Such cable guides can be sealed comparatively easily, so that even if the waveguide is completely immersed into the medium to be measured, no medium will get into the interior of the housing via the cable guide.

Furthermore, it is regarded as advantageous when the at least two guide elements are made of a non-piezoelectric material.

Furthermore, it is preferred for the operation of the waveguide that a thickness of one of the opposing guide elements is such that synchronous acoustic surface waves propagate both along the inner surface and along the outer surface of the respective guide element.

For the transmitter and/or the receiver of the apparatus according to the invention it is preferred that the same include a transducer, in particular a piezoelectric interdigital transducer. In particular, it can be provided that the transmitter and the receiver each are formed by a piezoelectric transducer with interdigital electrodes.

In addition, it can of course be provided that a plurality of transmitters and/or receivers is used and accommodated at and/or in the housing of the waveguide.

Preferably, the guide elements of the acoustic waveguide, on which the acoustic surface waves and the volumetric sound waves each are converted, include opposing flat plates or are completely formed from the same. The inner surfaces of the plate correspondingly are formed flat or planar.

In an alternative embodiment, however, the guide elements also can include at least one curved inner surface. The guide elements for example can be formed by opposing portions of a hollow cylinder or tube or include such portions, e.g. also be formed as a half shell each.

Further advantageous design variants of the apparatus according to the invention are also given be the sub-claims.

BRIEF DESCRIPTION OF THE DRAWINGS

Additional advantages and features will become apparent in the subsequent description of an exemplary embodiment.

FIG. 1 schematically shows an exemplary embodiment of a waveguide for the apparatus according to the invention, comprising two opposing plates extending parallel to each other as guide elements of the waveguide, which border an interior space to be filled with the medium to be measured.

DETAILED DESCRIPTION

In the sectional view of FIG. 1 an acoustic waveguide is shown with two (carrier) plates 1, 2 as guide elements of the waveguide. The plates 1 and 2, which are located opposite each other and extend parallel to each other along a direction of extension E of the waveguide, are made of a non-piezoelectric material. The plates 1 and 2 located opposite each other at a distance a furthermore border a (channel-shaped) interior space 5 of the waveguide, in which a medium L to be measured can be filled in or can flow through the interior space 5.

A flow direction of a fluid or flowable medium L through the interior space 5 in principle can be any direction and is determined by the formation of inlet and outlet openings at the housing G. In FIG. 1, the medium L might flow through e.g. along the direction of extension E and/or vertical thereto.

The two plates 1 and 2 of the waveguide of the apparatus according to the invention are fabricated integrally with a housing G of the waveguide, which accommodates both a transmitter 3 and a receiver 4 in its interior. Each of the plates 1, 2 is made integrally or in one piece with a housing portion G1 or G2 of the housing, which in the present sectional view form two housing halves of the housing G symmetrical to each other.

Both plates 1, 2 each have an inner surface 11, 21, which each faces the interior space 5 with the medium L and each forms an interface with the medium L. Inside each housing portion G1 and G2, there is furthermore formed an internal, completely enclosed cavity H1, H2, which each faces an outer surface 12, 22 of the plate 1 or 2, respectively. This outer surface 12, 22 is located opposite the inner surface 11, 21 of the respective plate 1, 2 and forms a side wall of the respective cavity H1, H2.

Inside the cavity H1 adjoining the (first) plate 1, the transmitter 3 is arranged. The transmitter 3 is a piezoelectric transducer with interdigital electrodes, which is fixed on the outer surface 12 of the plate 1. Preferably, fixing the transmitter 3 is effected by bonding, so that the same can be mounted quickly and easily.

The receiver 4 in turn is arranged in the cavity H2 adjoining the (second) plate 2 and is fixed on the outer surface 22 of this plate 2. The receiver 4 is located in the region of a first end of the waveguide, while the transmitter 3 is arranged in the region of another, second end of the waveguide and in the illustrated cross-sectional view the waveguide extends between these two ends along the direction of extension E.

Via the transmitter 3, acoustic surface waves S1 are generated in the first plate 1, as soon as (alternating) electric current is supplied to the transmitter 3. At the interface of the inner surface 11, a part of the energy of these generated acoustic surface waves is coupled into the medium L as volumetric sound wave S3 or is converted into volumetric sound waves S3 of the medium L.

The two plates 1, 2 preferably are made of a non-piezoelectric material and have a thickness d which is smaller than or equal to the wavelength of the generated acoustic surface waves. Possibly, the acoustic surface waves which propagate inside the plates 1, 2 include Lamb waves (or wave types in the transition region of Lamb waves and Rayleigh waves) which propagate both along the inner surface 11, 21 and along the outer surface 12, 22 of the respective plate 1, 2. In dependence on the thickness d of the plates 1, 2, the acoustic surface waves substantially will be present in the form of Lamb waves (d smaller than the wavelength of the acoustic surface waves) or in the form of waves from the transition region between Lamb waves and Rayleigh waves (d equal to the wavelength of the acoustic surface waves). In each case, the acoustic surface waves propagate along both surfaces 11, 12 and 21, 22 of the plates 1 and 2, respectively.

As illustrated in FIG. 1, acoustic surface waves S1 hence extend proceeding from the transmitter 3 along the direction of extension E of the first plate 1. A part of the sound wave energy of the acoustic surface waves running along the inner surface 11 of the first plate 1 is coupled into the medium L present inside the interior space 5, so that volumetric sound waves S3 are generated inside the medium L. A direction of propagation of these volumetric sound waves coupled in is inclined by a characteristic angle δ relative to a vertical reference line along the flat surface 11 of the first plate 1.

As soon as the volumetric sound wave S3 reaches the inner surface 21 of the opposing second plate 2, a part of its energy is coupled into the second plate 2, so that acoustic surface waves S2 (for example in the form of Lamb waves or surface waves in the transition region) are generated therein, which propagate along the direction of extension E of the second plate 2. The acoustic surface waves S2 of the second plate 2 also propagate both along the inner surface 21 and along the outer surface 22 of the second plate 2.

At each time at which the volumetric sound wave S3 reaches the inner surface 11 or 21 of the plates 1, 2, a part of its sound wave energy is coupled into the respective plate 1, 2 and acoustic surface waves S1, S2 are generated in the respective plate 1, 2. While the intensity of the volumetric sound waves S3 decreases on their zigzag-shaped path of propagation (in FIG. 1 designated with P2), the sound wave energy of the acoustic surface waves S1, S2 increases inside the plates 1, 2, since the sound wave energy of the medium L is coupled in along their path of propagation designated with P1.

As shown in FIG. 1, the volumetric sound wave S3, which has been coupled into the medium on the inner surface 11 of the first plate 1 under the angle δ, reaches the receiver 4 at a point of interaction 12''', in that it proceeds along the zigzag-shaped path of propagation P2 inside the medium L and its sound wave energy is coupled into the second plate 2 at the point of interaction 12'''.

In addition, a part of its sound wave energy still is coupled into the second plate 2 at a plurality of further points of interaction 12, 12' and 12'', so that here acoustic surface waves S2 are formed or amplified. In this way, the acoustic surface waves S2 propagate along the second plate 2 over a comparatively large distance, before they reach the receiver 4.

Via the difference in the running times of surface waves S2 reaching the receiver 4 along the path of propagation P1, characteristic properties of the medium L - here a fluid —can be determined by means of an evaluation unit 6 of the apparatus according to the invention, which is connected with the receiver 4. For this purpose, the receiver 4 generates and transmits one or more signals to the evaluation unit, when the receiver 4 detects acoustic surface waves S2 reaching the same.

On the basis of acoustic surface waves S2 or groups of surface waves S2 arriving at the receiver 4 one after the other, the sound velocity inside the medium L can be inferred. Since the measured running times of the acoustic surface waves S2 coupled in at the points of interaction I2, 12', 12'' and 12''' through the volumetric sound waves S3 are influenced by the properties of the medium L (in particular by the propagation velocity of the volumetric sound waves S3 inside the medium L and the magnitude of the angle δ), physical and/or chemical properties of the medium L to be measured can be determined in this way by the evaluation unit 6.

Analogously, different amplitudes of the acoustic surface waves S2 measured by the receiver 4 can be used for determining physical and/or chemical properties of the medium L.

If the housing G of the apparatus is equipped and provided for the purpose that the medium L to be measured flows through the interior space 5, it can furthermore be provided that by means of the apparatus a flow velocity of the medium L flowing through the interior space 5 can be determined. For example, the flow velocity of the medium has an influence on the running times of the acoustic surface waves S2 received by the receiver 4, so that the flow velocities can be inferred therefrom.

In a further embodiment, the housing G includes at least one transmitter 3 and one receiver 4, which both are associated to a guide element or a plate 1, 2, on whose inner surface 11, 21 acoustic surface waves S2 generated by the transmitter 3 can be converted into volumetric sound waves S3. In other words, for example, the transmitter 3 and a (possibly additional) receiver are arranged on a common guide element, for example the first plate 1 or the second plate 2. An additional receiver might be arranged on the outer surface 12 of the first plate 1 opposite the receiver 4 of the second plate 2 as shown in FIG. 1.

The apparatus now furthermore is formed and equipped to determine a temperature of the medium L by means of the acoustic surface waves S2 received by this receiver. This is possible, as in particular the velocity of the acoustic surface waves S2 along the guide element or the plate 1, 2, on which the transmitter 3 is arranged (here the first plate 1), substantially depends on the temperature of the medium L.

To avoid that the plates 1, 2 must be sealed with great effort against the cavity H1, H2 adjoining the same and accommodating the transmitter 3 or the receiver 4, the plates 1 and 2 are formed integrally with the respective housing portion G1, G2 and integrally with the housing G, in accordance with the invention. The cavities H1 and H2 for example can be formed by a material-removing, in particular machining manufacturing method, such as for example turning, milling or boring, from a solid material of the respective housing portion G1, G2. In doing so, the transmitter 3 or the receiver 4 are positioned inside the cavity H1, H2 via an insertion opening 7 or 8. Fixing the transmitter 3 and the receiver 4 on the outer surface 12, 22 of the associated plate 1, 2 preferably is effected by bonding.

The insertion opening 7 or 8, through which the transmitter 3 or receiver 4 can be introduced into the interior of the cavity H1, H2, preferably is located on an outside of the housing G. In other words, the insertion opening 7 or 8 just does not open into the interior space 5, in which the medium L to be measured is present or through which the medium L to be measured flows. Since the medium L in particular is an acidic or alkaline fluid, it is avoided in this way that a sealing of the insertion opening 7 or 8 (not shown) is directly exposed to the medium. A possible influence on the measurement by the waveguide shown cannot safely be excluded, when the insertion opening is not located on one of the plates 1, 2 and its inner (11, 21) or outer surfaces (12, 22), respectively, and hence for example adjacent to the interior space 5.

However, it can of course be provided that the waveguide shown with the housing G can completely be immersed into the medium L to be measured. The sealing of an insertion opening at the housing portions G1 and G2 then still can be realized more easily than would be the case with plates 1, 2 to be mounted separately on the respective housing portion G1, G2.

Furthermore, the insertion opening 7 or 8 can serve as cable guide, via which a line 9 or 10 is guided from the outside to the transmitter 3 or to the receiver 4. Such lines 9 and 10 can be provided both for supplying said electronic components with electric current, but such lines 9 and 10 can also be formed as data or control line, in order to control the function of the transmitter 3 or to transmit signals generated by the receiver 4 to the evaluation unit 6 located outside the housing G.

Likewise, a plurality of different lines can be guided out of the housing B from the respective cavity H1, H2 via a single common insertion opening.

Alternatively or in addition, an individual or a plurality of cable guides different from the insertion opening can be made in the housing G, via which the line is guided out from the housing G.

Furthermore, an electronic evaluation unit of the apparatus according to the invention can also be accommodated inside the housing G. In one development, the evaluation unit for example can be equipped and provided for storing the signals which have been transmitted by the receiver 4, and then after measuring the stored and possibly evaluated signals transmit the same via a connector provided at the housing G to a computer unit, such as a computer system.

In a further design variant, the transmitter 3 and the receiver 4 are already arranged in an injection molding die already before molding the housing G. By a corresponding design of the injection molding die, the (molding) material, from which the housing G is made, is introduced into the injection molding die in liquid form around the transmitter 3 and the receiver 4, so that the transmitter 3 and the receiver 4 each are fully enclosed by the material of the housing G.

The cavities H1 and H2 then for example already are provided in the injection molding die as female mold, so that after curing of the material of the housing G the transmitter 3 and the receiver 4 are enclosed in the respective cavity H1, H2, without a subsequent sealing of the respective cavity H1, H2 being necessary. Possibly, any lines can already be arranged in the injection molding die before filling in the liquid material for the housing G, so that the same already are embedded in the same during manufacture of the housing G and are guided to the outside from the interior of the respective cavity H1, H2.

In contrast to the representation of FIG. 1, the transmitter 3 and the receiver 4 also can at least partly be embedded inside the material for manufacturing the housing G.

For example, inside an injection molding die a receptacle or recess can be provided, into which the transmitter 3 or the receiver 4 can be inserted, so that when filling the liquid material for manufacturing the housing G into the injection molding die, the transmitter 3 or the receiver 4 is at least partly directly brought in contact with the liquid material. The curing material of the housing G hence forms a positive enclosure for the transmitter 3 and/or the receiver 4, so that its intended position inside the housing G can be ensured.

To furthermore be able to provide an air- or gas-filled cavity H1, H2 inside the housing G, which directly adjoins the outer surface 12, 22 of the plate 1, 2, it can be provided that the transmitter 3 or the receiver 4 in the design variant described above is only partly surrounded by the material of the housing G or is not completely embedded in the material of the housing G. For this purpose, the outer surface 12, 22 for example forms a cup- or pot-shaped receptacle in which the transmitter 3 or the receiver 4 is positively accommodated.

Such positive receptacle for the transmitter 3 and/or the receiver 4 can also be made inside a cavity H1, H2 by means of a material-removing method.

Alternatively, the transmitter 3 and/or the receiver 4 can completely be enclosed by material of the housing G, so that in this way no cavity H1, H2 is formed during the manufacture of the housing G or the cavity H1, H2 at least does not contain the transmitter 3 or the receiver 4.

In any case, it remains an essential aspect that the plate 1, 2 as guide element of the acoustic waveguide is integrally formed with the respective housing portion G1, G2, so that its surfaces facing the interior space 5 are active surfaces 11, 21 of the waveguide and the additional installation of seals for separately mountable plates 1, 2 can be omitted.

In contrast to the illustrated embodiment with flat plates 1, 2 as guide elements of the waveguide, the guide elements can be provided with curved inner surfaces. Such guide elements for example can be formed by curved, opposing tube portions, so that the interior space 5 bordered by the same substantially is designed tubular.

In a development of the exemplary embodiment of FIG. 1, it is also possible to use a plurality of transmitters 3 and/or a plurality of receivers 4 inside the apparatus according to the invention. The same can then be accommodated inside the housing G analogous to the shown transmitter 3 and the shown receiver 4 and analogous to the previous embodiments.

In one development of the illustrated apparatus, the distance a and/or the inclination of the two housing portions G1 and G2 relative to each other is (steplessly) adjustable. In this way, the dimensions and the shape of the interior space 5 accommodating the medium L can be variable.

The housing G preferably will be made of metal, for example of stainless steel, or of a plastic material, for example polyether ether ketone (PEEK) or polyoxyethylene (POM).

The invention claimed is:

1. An apparatus for determining the properties of a medium in the form of a fluid or a soft material, comprising:
    a) an acoustic waveguide which comprises at least two opposing guide elements which delimit an interior space to be filled with the medium and which upon filling the interior space with the medium each form an interface with the medium with an inner surface, b) a transmitter for generating acoustic surface waves in the waveguide, c) a receiver for receiving acoustic surface waves propagating along the waveguide, which is configured to be coupled with an evaluation unit for determining physical properties of the medium on the basis of a signal which is generated by the receiver upon receipt of the acoustic surface waves, and d) a housing, in or at which at least the guide elements, the transmitter and the receiver are accommodated, wherein on the respective inner surface at least a part of the acoustic surface waves are converted into volumetric sound waves of the medium and at least a part of the volumetric sound waves are converted into acoustic surface waves of the waveguide, and wherein the guide elements are integrally formed with the housing accommodating the transmitter and the receiver such that the guide elements are integrally formed with one another.

2. The apparatus according to claim 1, wherein on an outer surface of a guide opposite the inner surface the transmitter is arranged, the receiver is arranged, or both the transmitter and the receiver are arranged.

3. The apparatus according to claim 2, wherein the outer surface of a guide element borders a cavity of the housing in which the transmitter is accommodated, the receiver is accommodated, or both the transmitter and the receiver are accommodated.

4. The apparatus according to claim 3, wherein the cavity includes at least one insertion opening through which the transmitter, the receiver, or both the transmitter and the receiver are introduced into an interior region of the cavity.

5. The apparatus according to claim 3, wherein the cavity is made in the housing by a material-removing manufacturing method or by a casting method.

6. The apparatus according to claim 5, wherein the cavity is made by a casting method around the transmitter to be arranged therein, the receiver to be arranged therein, or both the transmitter and the receiver to be arranged therein.

7. The apparatus according to claim 3 wherein the cavity is sealed against an exterior space surrounding the housing.

8. The apparatus according to claim 1, wherein one or both of the transmitter and the receiver is embedded in a material from which the housing is made.

9. The apparatus according to claim 1, wherein the housing includes two housing portions each with one of the two opposing guide elements.

10. The apparatus according to claim 9, wherein a distance of the two housing portions from each other is adjustable, an inclination of the two housing portions relative to each other is adjustable, or both the distance and the inclination are adjustable.

11. The apparatus according to claim 1, wherein the housing is made of a metal or of a plastic material.

12. The apparatus according to claim 1 wherein the housing includes at least one cable guide via which a line is guided from the transmitter out of the housing, from the receiver out of the housing, or from both the transmitter and the receiver out of the housing.

13. The apparatus according to claim 1, wherein the at least two guide elements are made of a non-piezoelectric material.

14. The apparatus according to claim 1, wherein a thickness of at least one of the opposing guide elements is such that synchronous acoustic surface waves propagate both along the inner surface and along the outer surface of the guide element.

15. The apparatus according to claim 1, wherein one or both of the transmitter and the receiver include a transducer.

16. The apparatus according to claim 1, wherein the housing is equipped and provided for the purpose that the medium to be measured flows through the interior space.

17. The apparatus according to claim 16, wherein by means of the apparatus a flow velocity of the medium flowing through the interior space can be determined.

18. The apparatus according to claim 1, wherein the apparatus is formed and equipped to determine a temperature of the medium by means of the surface waves received by this receiver.

19. The apparatus according to claim 1, wherein the guide elements are formed as plates.

20. The apparatus according to claim 1, wherein the housing and the guide elements collectively form a unitary component devoid of seals between the housing and the guide elements.

* * * * *